United States Patent
Potts

(10) Patent No.: US 6,324,915 B1
(45) Date of Patent: Dec. 4, 2001

(54) DRIVING POINT IMPEDANCE HEAD FOR MEASUREMENT OF ELASTOMERIC MECHANICAL PROPERTIES

(75) Inventor: Gerald R. Potts, Fairlawn, OH (US)

(73) Assignee: Test Measurements Systems Inc., OH (US)

( * ) Notice: Subject to any disclaimer, the term of this patent is extended or adjusted under 35 U.S.C. 154(b) by 0 days.

(21) Appl. No.: 09/454,320

(22) Filed: Dec. 3, 1999

(51) Int. Cl.[7] .................................................. G01N 3/32
(52) U.S. Cl. ................................................................ 73/808
(58) Field of Search ................................ 73/805, 806, 808, 73/812, 815, 818, 826, 841, 844

(56) References Cited

U.S. PATENT DOCUMENTS

| 4,461,177 | * | 7/1984 | Feng | 73/587 |
| 4,546,658 | * | 10/1985 | Rocha et al. | 73/862.59 |
| 4,633,718 | * | 1/1987 | Van Engelshoven | 73/822 |
| 5,033,308 | * | 7/1991 | Le Compagnon et al. | 73/788 |
| 5,877,428 | * | 3/1999 | Scolton | 73/822 |

* cited by examiner

Primary Examiner—Max Noori
(74) Attorney, Agent, or Firm—Arter & Hadden LLP

(57) ABSTRACT

Methods and systems for measurement of mechanical properties of elastomeric materials use a driving point impedance head such as a load cell instrumented hammer to apply forces to a force distribution mass positioned over a test specimen upon a rigid base. Broad frequency responses of the driving point impedance head reveal elastic and viscous moduli response frequencies from 0 Hz to 2000 Hz. Methods and systems for measuring responses of elastomeric materials under a preload are also disclosed.

20 Claims, 10 Drawing Sheets

DRIVING POINT IMPEDANCE HEAD FOR MEASUREMENT OF ELASTOMERIC MECHANICAL PROPERTIES

FIELD OF THE INVENTION

The invention pertains generally to methods and systems for measuring forces and, more particularly, to methods and systems for measuring mechanical properties of elastomeric materials.

BACKGROUND OF THE INVENTION

Conventional methods for testing the mechanical properties of elastomeric materials, such as rubber and urethanes, seek to determine elastic and viscous moduli by vibrating specimens at different frequencies. For example, to find the elastic and loss bulk moduli of an elastomeric specimen with dimensions 5 inches in diameter and ½ inch in. thickness (circular disk-flat), these moduli should be functions of excitation frequency over a range of 0–2000 Hz.

As shown in FIG. 1A, a typical measuring technique is to use a Universal Test Machine (UTM) loading frame 10 to apply loads and capture data. The UTM 10 includes an upper crosshead 12 that supports a load cell 14 and is connected to a base crosshead 16, stably affixed to a floor mounted base 18. A flat disc specimen 20 is placed on top a hydraulic actuator 22, which imparts a forcing function to the specimen.

Using Fourier analysis, this forcing function can be regarded as comprising a range of excitation frequencies. The forcing function is measured by the load cell 14 as f(t). As seen in FIG. 1B, the load cell 14 measures time-varying input motions from a displacement x(t) in the specimen 20, in order to derive an elastic spring force proportionality rate k, and a viscous damping force proportionality rate c.

Forces generated and transmitted to the load cell are given as:

$f(t) = cx + kx$

A Fourier Transform to the frequency domain yields:

$F(\omega) = (k + j\omega c)\overline{X}(\omega)$ and a formulation of the Frequency Response Function (FRF):

$$\frac{F(\omega)}{\overline{X}(\omega)} = k + j\omega c$$

shows that the real part represents the elastic spring rate and the imaginary part contains the damping rate times the frequency.

This method yields worthwhile results until f(t) begins to contain forces with sources other than those transmitted by the elastomer, for instance mechanical resonances of the machine parts. Results at frequencies above that point are unreliable. Dynamic force measurement (DFM) techniques may be used to remove the resonant effects from the f(t) data. However, neither method yields wide band frequency results directly.

SUMMARY OF THE INVENTION

In view of the difficulties and drawbacks associated with previous methods and apparatuses, there is therefore a need for a test measurement apparatus that can measure results more directly.

There is also a need for a test measurement apparatus that can measure frequency response over a larger frequency range and that is less sensitive to vibrations from external sources.

These needs and others are satisfied by the present invention in which a test measuring device is provided including a base for supporting an elastomeric sample to be measured. A driving point impedance head is provided for imparting a force. A force distributing member receives the imparted force and applies it to the sample. One or more sensors are attached to the force distributing member, for measuring the frequency response of the mass to the imparted force. An analytical device is provided for transforming the frequency response to obtain correlated values representing elastomeric properties of the sample.

As will be realized, the invention is capable of other and different embodiments and its several details are capable of modifications in various respects, all without departing from the invention. Accordingly, the drawing and description are to be regarded as illustrative in nature and not restrictive.

DETAILED DESCRIPTION OF THE INVENTION

Figure 1A:
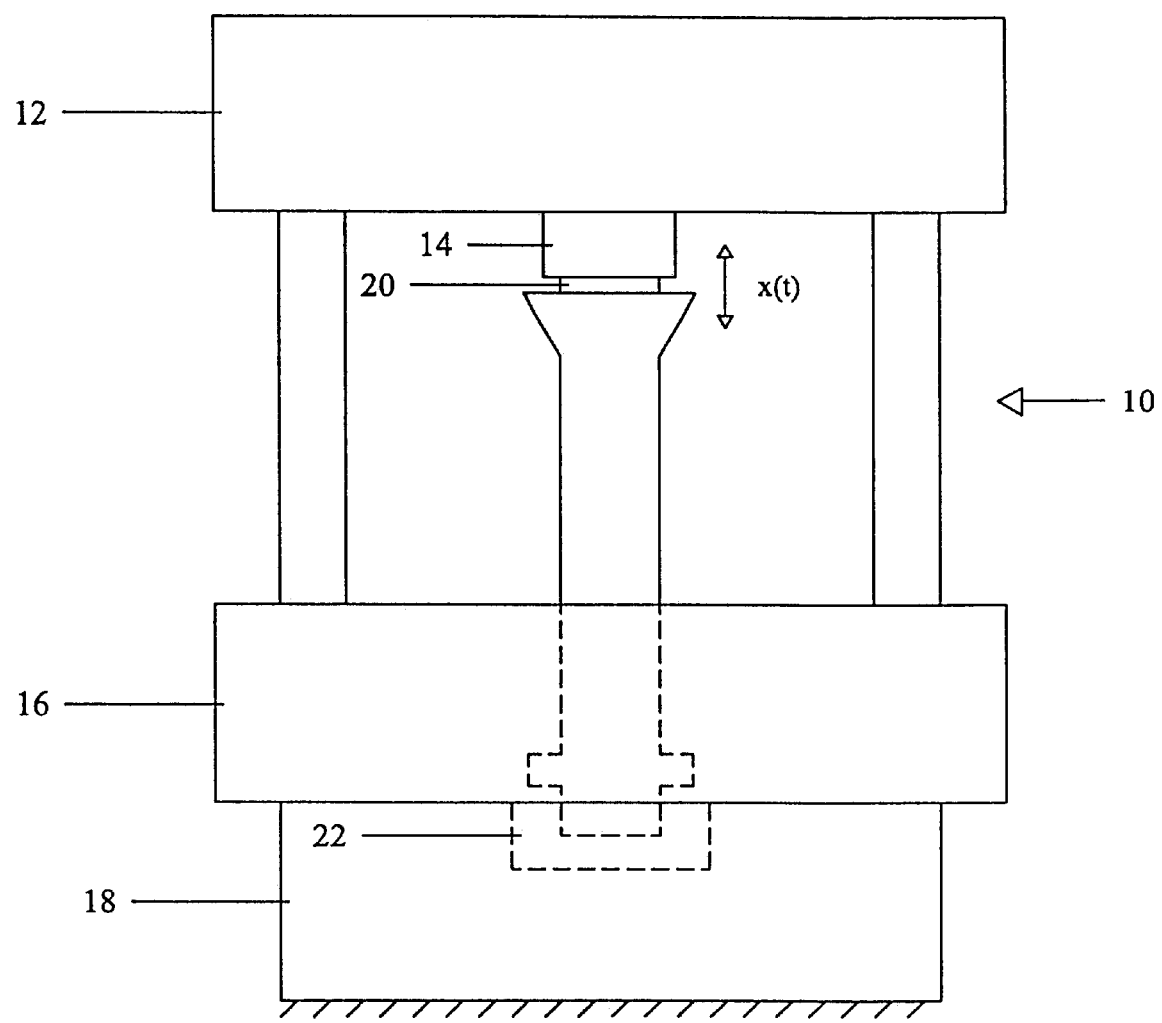
FIGS. 1A and 1B are side views respectively showing a previous-type test measurement apparatus and detail on the load cell.
Figure 1B:
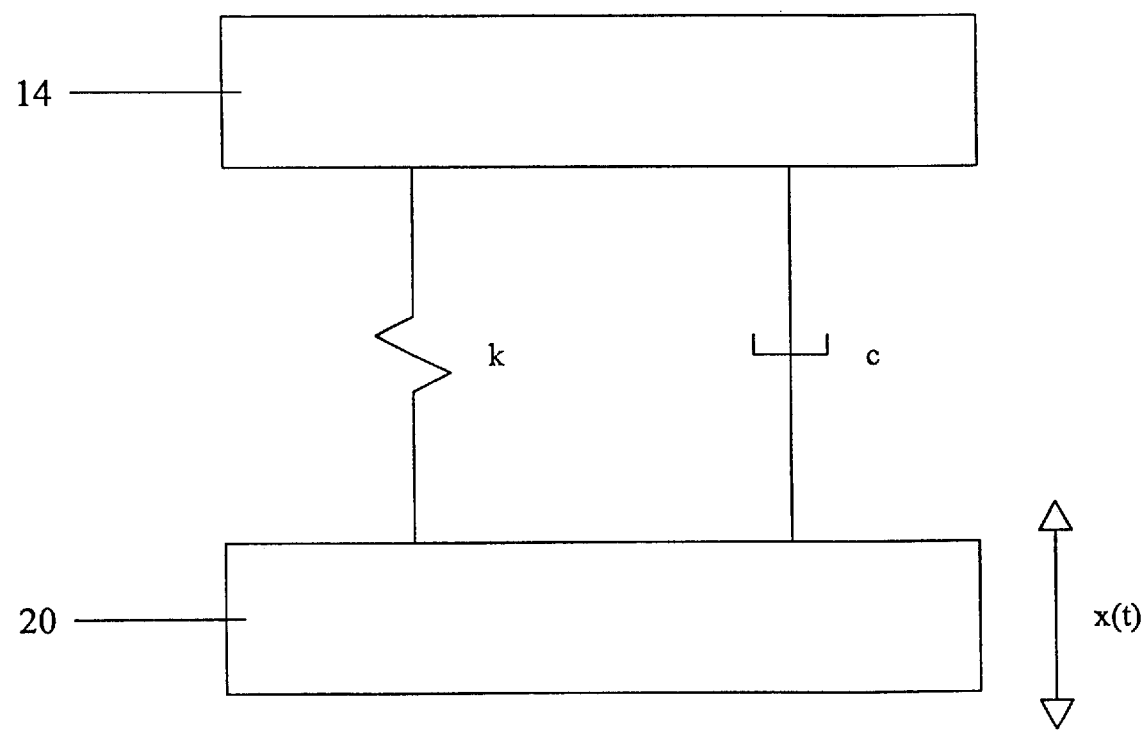
Figure 2A:
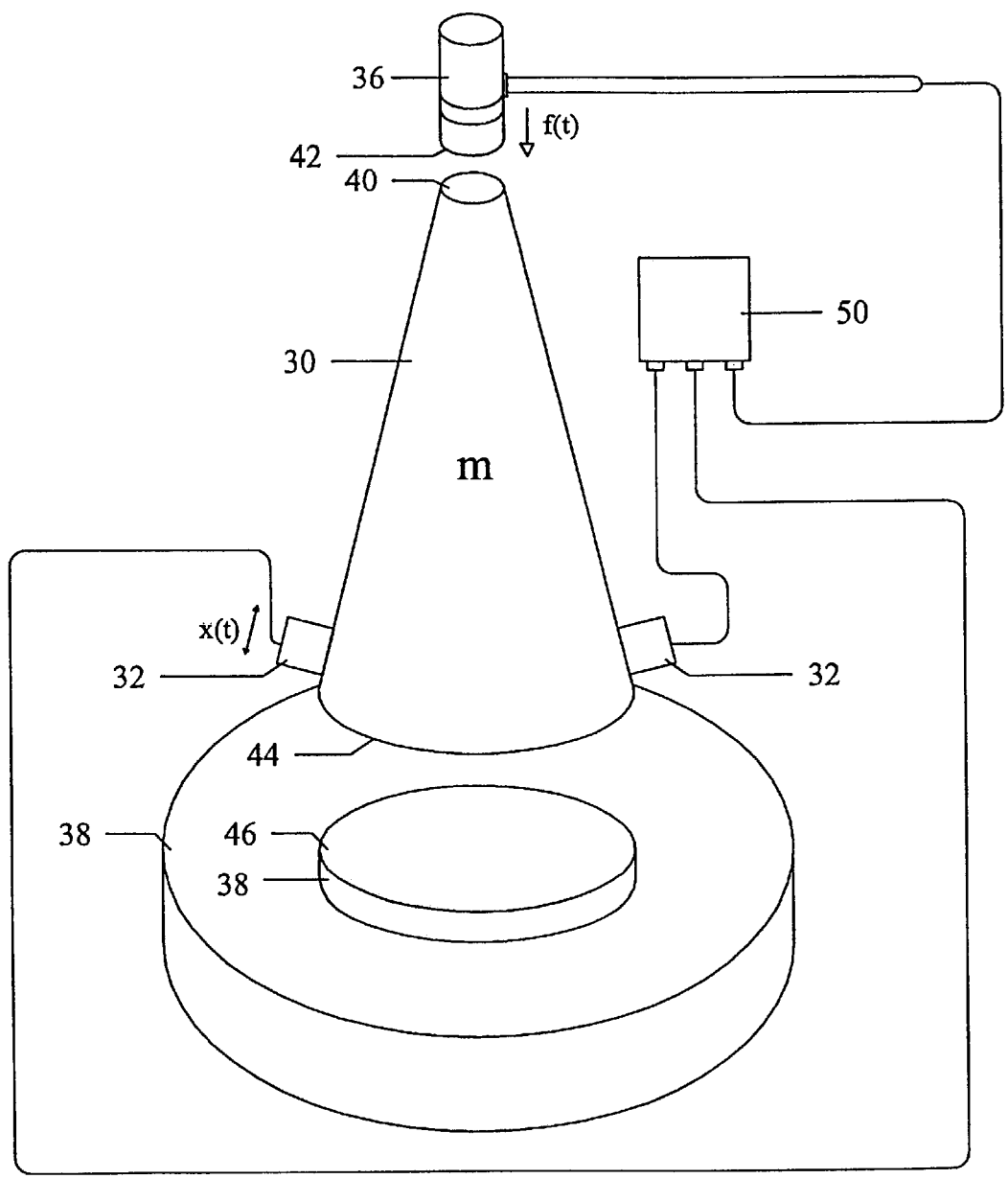
FIGS. 2A, 2B and 2C are respective oblique and side views showing the general configuration of the present invention, with a free-body diagram depicting the forces applied to the mass 30.
Figure 2B:
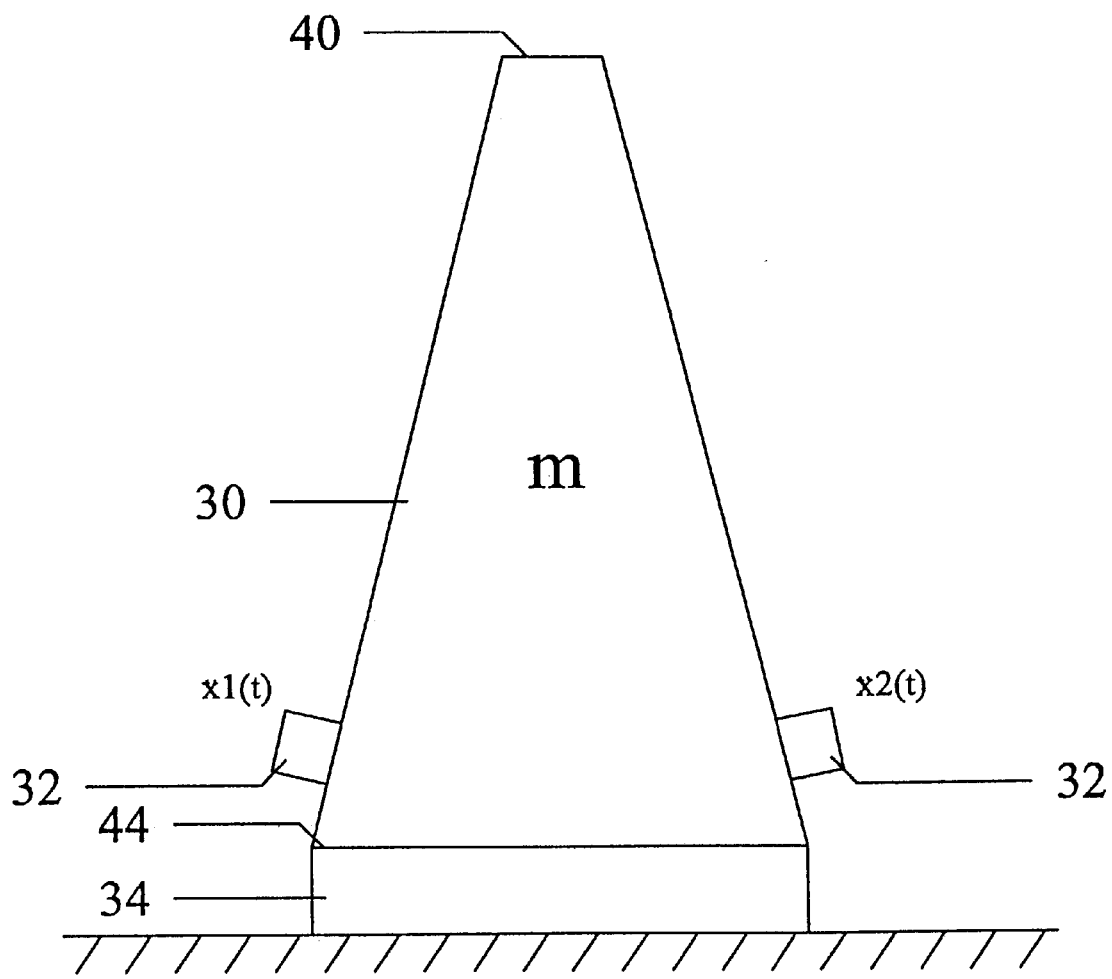
Figure 2C:
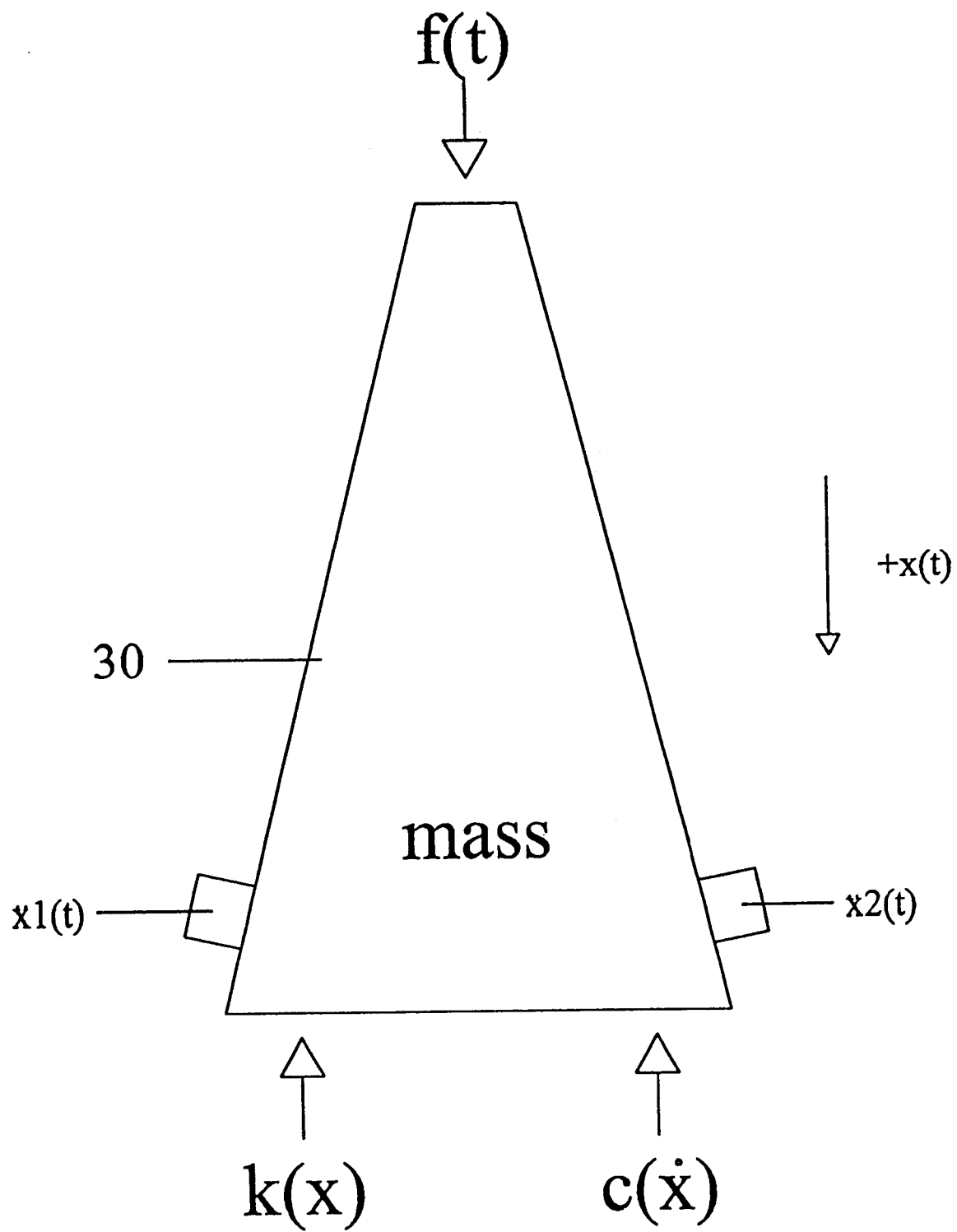

The present invention provides improved methods and systems for measuring the elastic and viscous moduli of elastomeric materials through a frequency range as high as 2000 Hz. In a general aspect of the invention, as shown in FIGS. 2A, 2B and 2C, a force distributing mass 30, in for example a conical or spherical shape, having one or more attached sensors, preferably accelerometers 32, is placed over a test specimen 34 and struck with a driving point impedance head, i.e. a load cell instrumented hammer 36. The hammer impact force f(t) contains a broad spectrum of frequencies in a range from low to high frequencies. The specimen or sample 34 can be e.g. five inches in diameter. The sample rests on a flat, solid base 38, which can be a cast iron machine tool bed or a thick granite base. In another general aspect of the invention, as will be discussed below, methods and systems are provided for measuring the mechanical response of a specimen 34 under a pre-load, which is compensated for in the force measurement methodology.

As can be seen in FIG. 2A, the mass 30 has a first contact surface 40 substantially sized to the striking surface 42 of the hammer 36. A second contact surface 44 is substantially sized to an impact surface 46 of the sample 34. As can be seen, the first contact surface 40 is smaller than the second contact surface, in order to distribute the force of the hammer 36. In a conical mass 30, the mass is conically tapered from the first contact surface to the second contact surface. However, for a spherical mass 30, the force distributing member 30 is radially curved between the surfaces.

The accelerometers 32 are connected to a processing unit 50, which monitors hammer force input and acceleration response of the mass 30.

FIGS. 2B and 2C show a free Body diagram of forces applied to the conical mass. Each accelerometer 32 measures time-dependent accelerations $(\ddot{x}_1(t), \ddot{x}_2(t))$ on each side of the mass or force distributing member 30. The processing unit 50 calculates the total acceleration $\ddot{x}(t)$ as:

$$\ddot{x}(t) = \frac{(\ddot{x}_1(t) + \ddot{x}_2(t))}{2\cos\Theta}$$

where $\Theta$ is the inclination angle of the accelerometer to the impacting force.

As the mass m of the member 30 is known, combined with the measured acceleration, the total forces of the system can be given as:

$$\Sigma F = f(t) - c\dot{x} - kx = m\ddot{x}$$

and the hammer force can be written as:

$$m\ddot{x} + m\dot{x} + kx = f(t) \quad (1)$$

The processing unit 50, such as an appropriately programmed microprocessor, operatively connected to the accelelerometers, performs a Fourier Transform, algorithm as before, which yields:

$$[(k - \omega^2 m) + j\omega c]\bar{X}(\omega) = F(\omega) \quad (2)$$

$$-\omega^2 \bar{X}(\omega) = FFT \text{ of } \ddot{x}(t)$$

Taking the real part of the Frequency Response Function:

$$(k - \omega^2 m) = \text{Re}\left[\frac{F(\omega)}{X(\omega)}\right]$$

which yields:

$$k = \text{Re}\left[\frac{F(\omega)}{X(\omega)}\right] + \omega^2 m \quad \text{and} \quad (3)$$

$$c = \frac{1}{\omega} \cdot \text{Im}\left[\frac{F(\omega)}{X(\omega)}\right] \quad (4)$$

In this way, the spring and damping rates can be derived and connected to material properties, such as elastic and loss moduli of the materials. While a number of algorithms can be used to derive these and other mechanical properties from the derived spring and damping constants without departing from the invention, an exemplary algorithm is given as follows:

$$\varepsilon_x = \frac{1}{E} * [\sigma_x - v(\sigma_y + \sigma_z)]$$

$$\varepsilon_y = \frac{1}{E} * [\sigma_y - v(\sigma_x + \sigma_z)] \quad \text{Hooke's law for compression only}$$

$$\varepsilon_z = \frac{1}{E} * [\sigma_z - v(\sigma_x + \sigma_y)]$$

$$\text{Dilatation, } l = \frac{(1 - 2v)}{E}(\sigma_x + \sigma_y + \sigma_z)$$

Which simplifies to $$l = \frac{3(1 - 2v)}{E}\sigma_m$$

where $\sigma_m$=mean stress, or hydrostatic pressure or
$\sigma_m$=Kl $$\text{dilatation, } l = \frac{\Delta V}{V}$$

$$\text{Bulk Modulus, } K = \frac{E}{3(1 - 2v)}$$

also, from Hooke's Law $$\varepsilon_z = \frac{1}{E} * [\sigma_z - v(\sigma_x + \sigma_y)]$$

for hydrostatic stress $$\frac{\delta}{L} = \frac{1}{E}\left[\frac{F}{A} - v\left(\frac{2F}{A}\right)\right] = \frac{F}{EA}(1 - 2v)$$

where
$\delta$ is the deflection of the specimen also
$F = k\delta$ so $$\frac{1}{L} = \frac{k}{EA}(1 - 2v) \quad \text{and} \quad E = \frac{kL}{A}(1 - 2v),$$

substitute into K, above, so that the bulk modulus K can be expressed as:

$$K = \frac{E}{3(1 - 2v)} = \frac{kL}{3A}$$

where
L is the disk height
A is the disk Area
k is from equation (3) also $$K' = \frac{cL}{3A}$$

for the loss modulus K'.

In this way, bulk and loss moduli can be easily derived using a relatively simple apparatus with straightforward algorithms. The frequency range for hammer impacts is as high as 10 kHz, so 2 kHz measurements are attainable. Smaller specimen sizes may be required in order to insure good frequency transmission through the conical mass and into the elastomeric sample disk 34. For instance, the frequency range of interest (e.g., 0–2000 Hz) must not include flexible-body resonant modes of the conical mass.

In a method of the invention, test results on a specimen are obtained by averaging over a plurality of impacts of an instrumented hammer upon a force distribution mass, for example 20 to 150 impacts. Stresses inside the sample 34 can be made more nearly hydrostatic by curing the disk inside of a steel ring to constrain radial growth during hammer impacts.

Figure 5A:
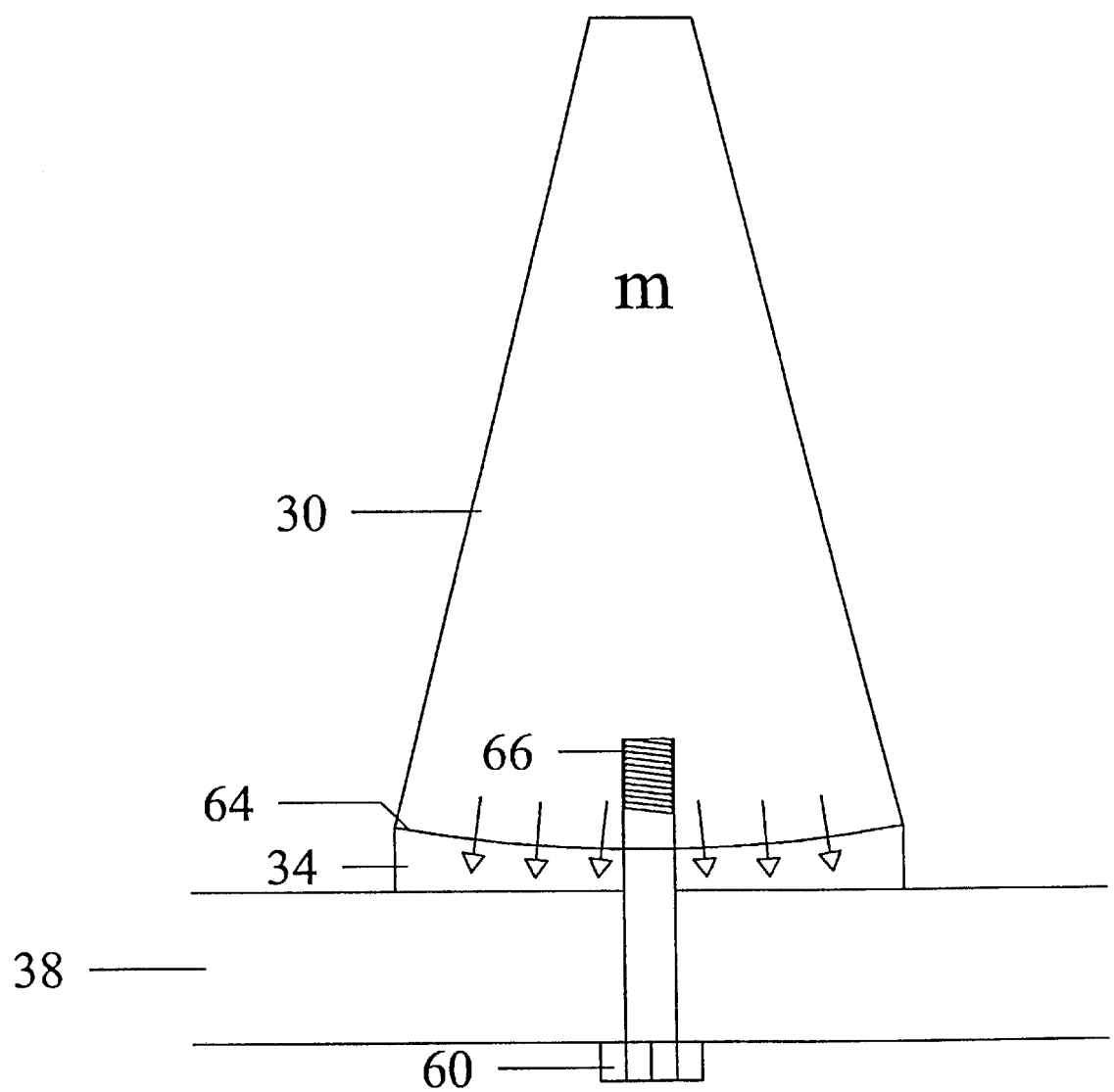
FIGS. 5A, 5B and 5C are side sectional views showing another alternate embodiment of the present invention.
Figure 5B:
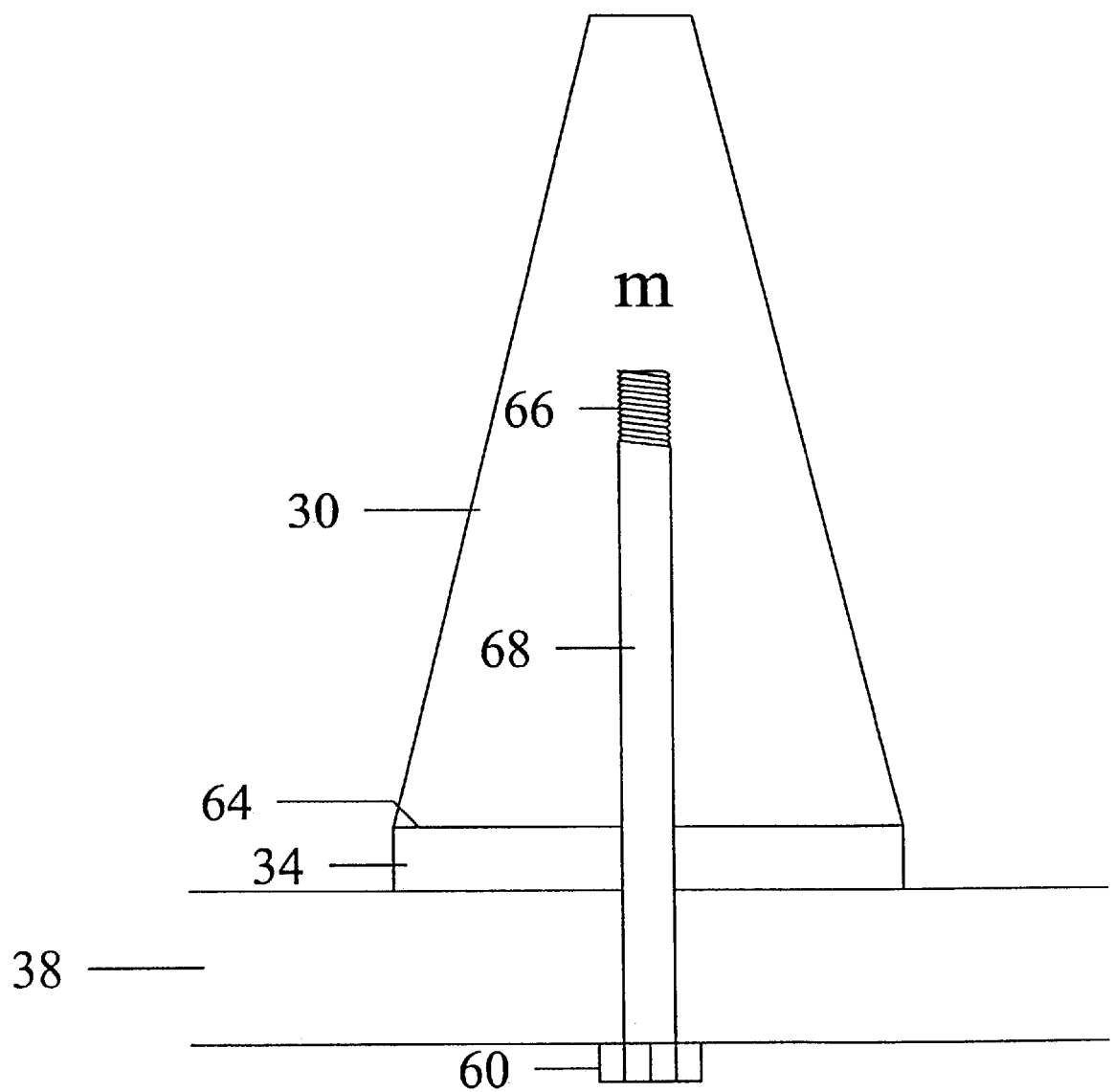
Figure 5C:
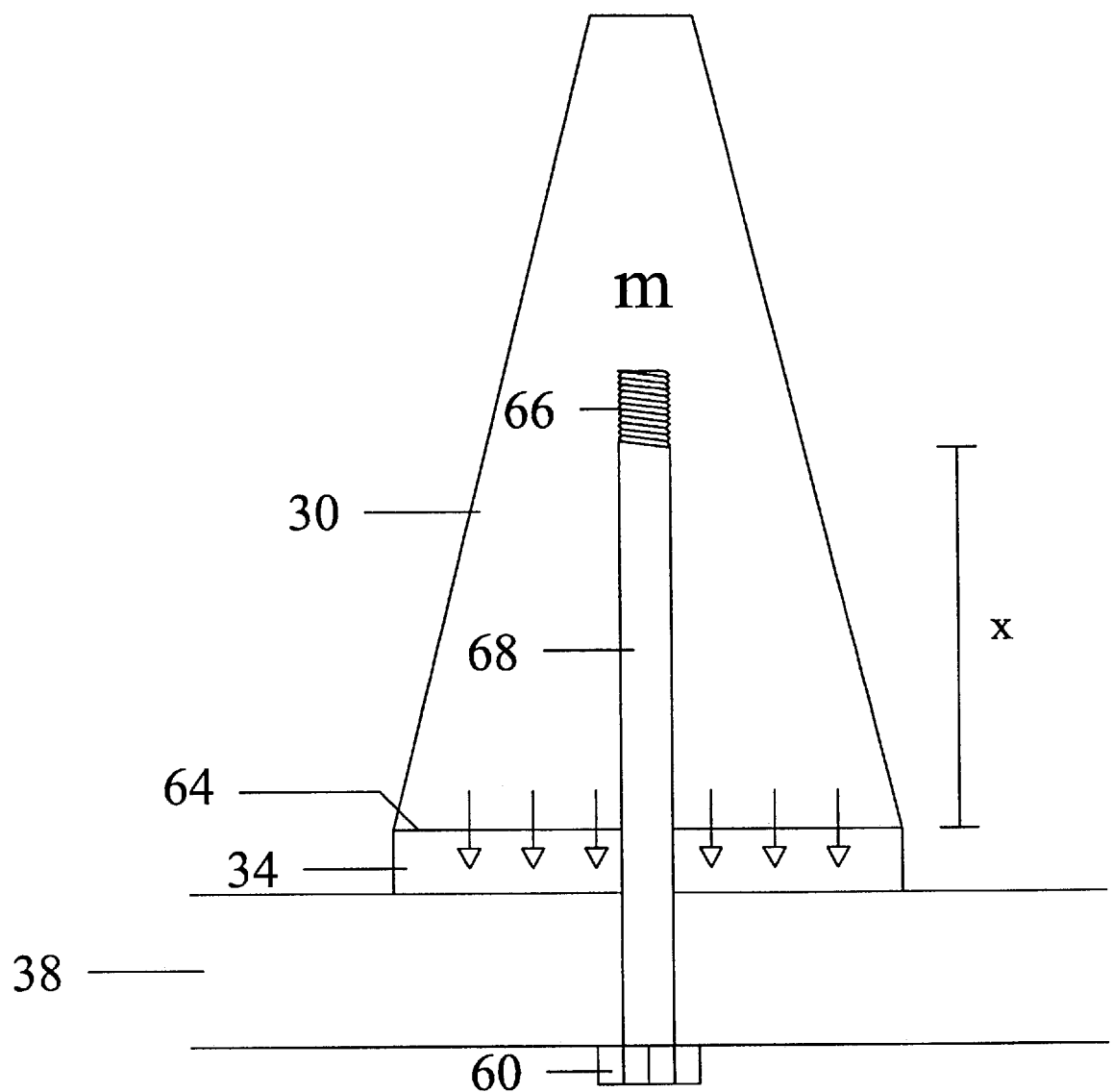

In another aspect of the invention, the conical mass 30 may be preloaded against the disk by fabricating a small load frame actuated by air springs and in order to provide a constant preload during hammer impact. As shown in FIGS. 5A, 5B and 5C, this can be done by sandwiching the test specimen 34 between the mass 30 and the Table 38 with an instrumented bolt 60, and instrumenting the bolt to read both the preload force and the force variation during hammer impact testing.

Figure 4A:
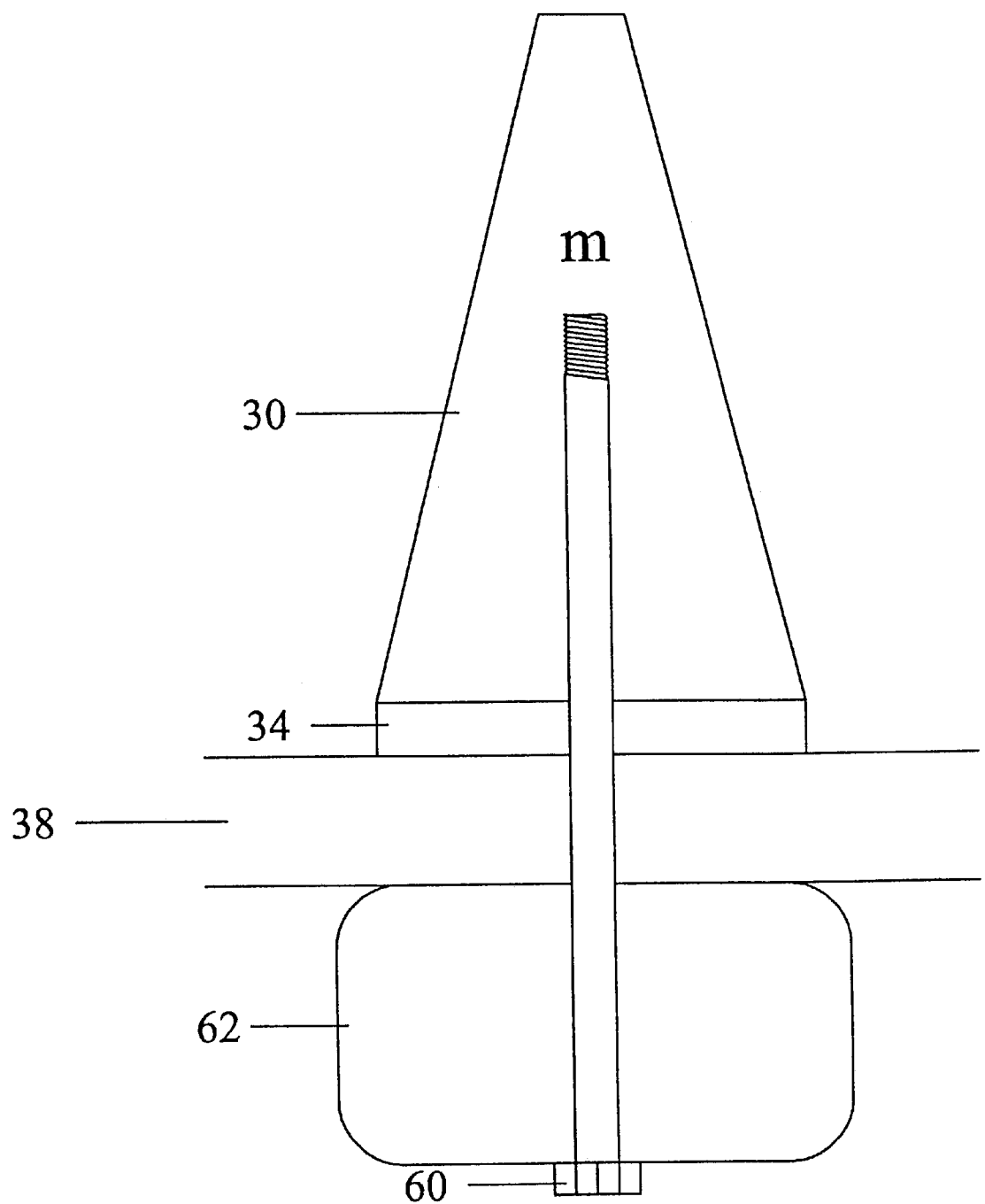
FIGS. 4A and 4B are side views showing alternate embodiments of the present invention.
Figure 4B:
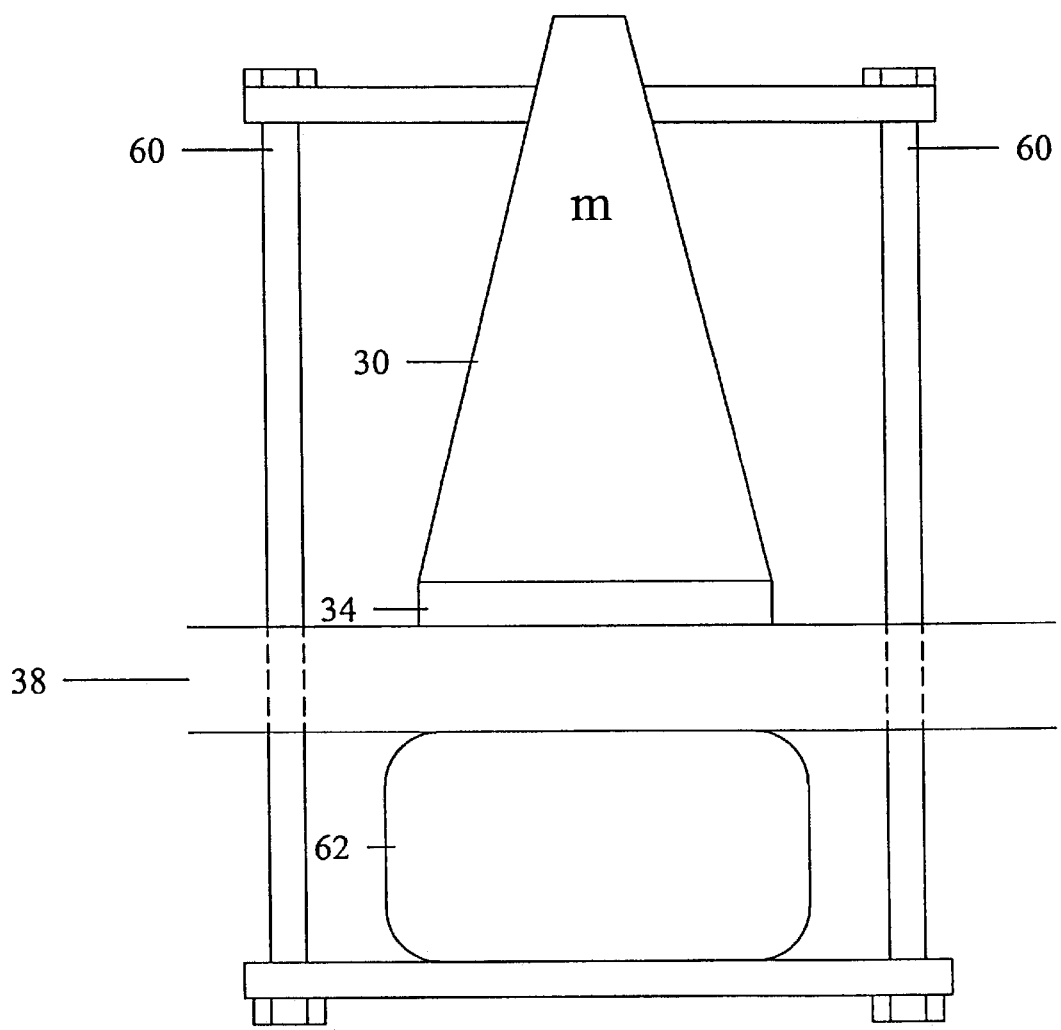

As shown in FIG. 4A, another method of applying a preload to an elastomeric test specimen uses a somewhat longer bolt 60, and an air spring 62 in order to keep the bolt tension nearly constant during the hammer impact. If the test specimen 34 cannot be altered by the bolt hole through the center, then a cage of 4–6 bolts 60 may be located about the periphery of the cone mass 30, symmetrically about the circumference of the specimen 34, as shown in FIG. 4B. With this arrangement, the mass m in the F=ma equation shown above needs to be increased to include the preload tooling; bolts, bolting ears and bottom plate. The frequency response with this arrangement will likely be lower than with any of the above.

As shown in FIG. 5A, to combat localized distortion due to localized force distribution at the cone/specimen interface 64 at the bolt, a radially tapered threading receptor portion 66 may be used to provide a more even force distribution. Also, as shown in FIGS. 5B and 5C, a more even force distribution may be achieved by moving the threading receptor 66 up into the center of the cone 30, away from the cone/specimen interface 64, and providing a non-threaded clearance portion 68, where x is the distance the beginning receptor threads are recessed into the cone.

Also, it will be appreciated that the exact form of the mass m is not critical to the invention. Any shape which can transfer a localized force as applied for example by a hammer to a broader area can be employed. For example, a spherical shape, or other generally conical shapes with a rounded or truncated apex point are also suitable.

As described hereinabove, the present invention solves many problems associated with previous type products. However, it will be appreciated that various changes in the details, materials and arrangements of parts which have been herein described and illustrated in order to explain the nature of the invention may be made by those skilled in the art within the principle and scope of the invention will be expressed in the appended claims.

I claim:

1. A measuring device comprising:
   a base for supporting an elastomeric sample to be measured;
   a driving point impedance head for imparting a force to a sample;
   a force distributing member for receiving the imparted force and applying it to the sample;
   at least one sensor, attached to the force distributing member, for measuring the frequency response of the force distributing member to the imparted force; and
   means for transforming the frequency response to obtain correlated values representing elastomeric properties of the sample, wherein the sensor includes an accelerometer for measuring time-dependent accelerations in the force distributing member to derive the frequency response of the load distribution mass, which drives the sample.

2. The device of claim 1 wherein the base is a flat solid base.

3. The device of claim 2 wherein the base is one of a cast iron machine tool bed and a thick granite base.

4. The device of claim 1 wherein the driving point impedance head is a load cell instrumented hammer that applies a predetermined force.

5. The device of claim 4 wherein the load cell instrumented hammer is supported in a crosshead assembly connected to the base.

6. The device of claim 1 wherein the force distributing member has a first contact surface substantially sized to a respective striking surface on the hammer, and a second contact surface substantially sized to a respective impact surface on the sample.

7. The device of claim 6 wherein the first contact surface is smaller than the second contact surface.

8. The device of claim 7 wherein the force distributing member is conically tapered from the first contact surface to the second contact surface.

9. The device of claim 7 wherein the force distributing member is radially curved from the first contact surface to the second contact surface.

10. The device of claim 1 further comprising at least one bolt connected to the base and to the force distributing member, for uniform distribution of the applied force.

11. The device of claim 10 wherein at least one bolt comprises a cage of bolts threaded around the periphery of the force distributing member.

12. The device of claim 10 wherein at least one bolt is threaded from the base, through the sample, and into a threaded portion substantially along the center of the force distributing member.

13. The device of claim 12 wherein the threaded portion is substantially displaced from a surface in contact with the sample.

14. A method of measuring the mechanical properties of elastomeric materials comprising:
   providing a sample of elastomeric material;
   applying a distributed force to the surface of the sample;
   measuring the frequency response of the sample to the imparted force;
   transforming the frequency response to obtain correlated values representing elastomeric properties of the sample, the step of measuring comprises measuring time-dependent accelerations of a mass in contact with the sample, to derive the frequency response of the sample.

15. A method of determining an elastomeric property of a material, comprising of the steps of:
   providing a sample of material;
   applying a distributed force through a mass to the sample;
   measuring time-dependent accelerations of a mass in contact with the sample, and
   transforming the measured time-dependent accelerations of the mass to determine elastomeric properties of the sample.

16. The device of claim 1 wherein the means for transforming performs a Fourier-transform-based algorithm to derive the elastic and loss moduli of the elastomeric sample.

17. The method of claim 16 wherein the distributed force is a predetermined force distributed over a contact surface of the sample.

18. The method of claim 16 wherein the step of measuring comprises measuring time-dependent accelerations of a mass in contact with the sample, to derive the frequency response of the sample.

19. The method of claim 16 wherein the step of transforming comprises performing a Fourier-transform-based algorithm to derive the elastic and loss moduli of the elastomeric sample.

20. The method of claim 16 further comprising repeating the steps a predetermined number of times, to obtain a respective average of correlated values representing the elastomeric properties of the sample.

* * * * *